(12) United States Patent
Shinohara et al.

(10) Patent No.: US 11,253,160 B2
(45) Date of Patent: Feb. 22, 2022

(54) MEASURING APPARATUS AND BLOOD PRESSURE MEASURING METHOD

(71) Applicant: Nihon Kohden Corporation, Tokyo (JP)

(72) Inventors: Ryo Shinohara, Tokorozawa (JP); Kazuri Higashi, Tokorozawa (JP); Yukio Koyama, Tokorozawa (JP)

(73) Assignee: NIHON KOHDEN CORPORATION, Toyko (JP)

( * ) Notice: Subject to any disclaimer, the term of this patent is extended or adjusted under 35 U.S.C. 154(b) by 901 days.

(21) Appl. No.: 15/964,341

(22) Filed: Apr. 27, 2018

(65) Prior Publication Data

US 2018/0325393 A1 Nov. 15, 2018

(30) Foreign Application Priority Data

May 9, 2017 (JP) .............................. JP2017-092966

(51) Int. Cl.
*A61B 5/0215* (2006.01)
*A61B 5/00* (2006.01)
*A61B 5/021* (2006.01)

(52) U.S. Cl.
CPC ........ *A61B 5/02156* (2013.01); *A61B 5/0215* (2013.01); *A61B 5/02158* (2013.01); *A61B 5/6852* (2013.01); *A61B 5/741* (2013.01); *A61B 5/742* (2013.01); *A61B 5/7405* (2013.01); *A61B 5/746* (2013.01); *A61B 5/02108* (2013.01); *A61B 5/6851* (2013.01); *A61B 2560/0223* (2013.01)

(58) Field of Classification Search
None
See application file for complete search history.

(56) References Cited

U.S. PATENT DOCUMENTS

2012/0289808 A1 11/2012 Hübinette
2013/0285812 A1* 10/2013 Rantala .................. A61B 5/746
340/573.1

FOREIGN PATENT DOCUMENTS

EP 3 017 756 A1 11/2016
JP 2013-517863 A 5/2013

OTHER PUBLICATIONS

Extended European Search Report issued in Patent Application No. EP 18 17 0065.9 dated Sep. 28, 2018.

* cited by examiner

*Primary Examiner* — Michael R Bloch
(74) *Attorney, Agent, or Firm* — Pearne & Gordon LLP

(57) ABSTRACT

A measuring apparatus includes: a measuring section which performs an invasive blood pressure measurement, and which detects that a predetermined abnormal condition occurs in a blood pressure during the measurement; a detector which detects whether or not a zero point calibration is being executed on a transducer to be used in the measurement; and a notification controller which, in a case where the blood pressure measured by the measuring section is in the predetermined abnormal condition, controls whether an alarm is output or not, based on a detection state of the detector. The notification controller can select a first mode in which an alarm sound is output, or a second mode in which the alarm sound is not output, based on an elapsed time period from a predetermined timing relating to the zero point calibration, and an output from the measuring section.

6 Claims, 8 Drawing Sheets

MEASURING APPARATUS AND BLOOD PRESSURE MEASURING METHOD

CROSS-REFERENCE TO RELATED APPLICATION(S)

This application is based upon and claims the benefit of priority from prior Japanese patent application No. 2017-092966, filed on May 9, 2017, the entire contents of which are incorporated herein by reference.

BACKGROUND

The presently disclosed subject matter relates to a measuring apparatus and a blood pressure measuring method.

There is available an invasive blood pressure measuring method in which a catheter or the like is inserted into the blood vessel of the subject to continuously measure the time varying blood pressure (for example, see JP-T-2013-517863). The pressure generated in the blood vessel is converted to an electrical signal by a transducer which is connected to the catheter. A blood pressure monitor displays the blood pressure value and waveform corresponding to the electrical signal which has been converted by the transducer, to a medical person or the like.

In an invasive blood pressure measurement, it is necessary to perform a process called the zero point calibration for setting a reference value of the measurement. The zero point calibration is performed in the following manner. The transducer is placed in a reference point. When a pressure acting on the transducer is made zero (when the catheter is opened to the atmosphere), the electrical signal indicative of the blood pressure value is set to have a measurement reference value (for example, 0 mmHg).

In the case where an invasive blood pressure measurement is performed, it is recommended to output an alarm indicative of detachment of a catheter attached to the patient. When referring to the alarm, the medical person can immediately recognize the catheter detachment.

In the related-art blood pressure measuring system, as described above, an alarm function is disposed which, in the case where the situation meets given conditions, such as that where catheter detachment is detected informs the medical person of a predetermined abnormal condition (for example, a condition where the pulse cannot be detected, and the mean blood pressure is equal to or lower than 100 mmHg).

In the related-art blood pressure measuring system, however, there is a case where, after the zero point calibration for setting a reference value of the measurement is performed, an alarm sound is output, for example, although when a surgical operation remains under preparation. That is, there is a case where an alarm sound is wastefully generated after the zero point calibration. In this case, the medical person must perform an operation of cancelling the alarm sound. This operation disturbs other preparation works, and therefore is undesirable.

SUMMARY

The presently disclosed subject matter may provide a measuring apparatus and a blood pressure measuring method in which an alarm sound can be adequately output even in the case where the zero point calibration is performed.

The measuring apparatus may comprise: a measuring section which is configured to perform an invasive blood pressure measurement, and which is configured to detect that a predetermined abnormal condition occurs in a blood pressure during the invasive blood pressure measurement; a detector which is configured to detect whether or not a zero point calibration is being executed on a transducer that is to be used in the invasive blood pressure measurement; and a notification controller which, in a case where the blood pressure measured by the measuring section is in the predetermined abnormal condition, is configured to control whether an alarm is output or not, based on a detection state of the detector, wherein the notification controller can select a first mode in which an alarm sound is output, or a second mode in which the alarm sound is not output, based on an elapsed time period from a predetermined timing relating to the zero point calibration, and an output from the measuring section.

DETAILED DESCRIPTION OF EXEMPLARY EMBODIMENTS

Figure 1:
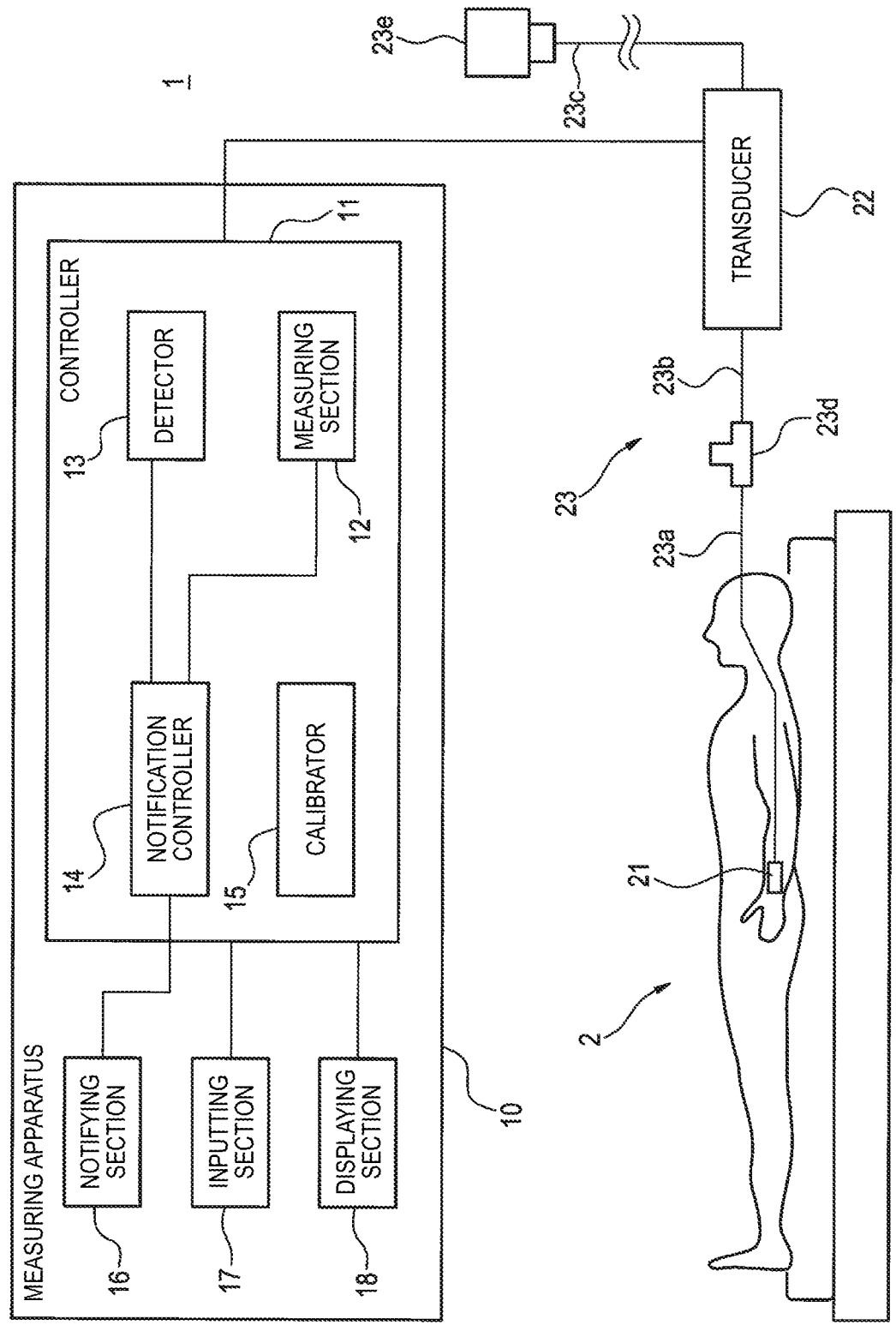
FIG. 1 is a diagram of a blood pressure measuring system including a measuring apparatus of an embodiment.

Hereinafter, a measuring apparatus of an embodiment will be described with reference to the drawing.

FIG. 1 is a diagram illustrating the configuration of a blood pressure measuring system 1 including the measuring apparatus 10 of the embodiment.

The blood pressure measuring system 1 can invasively measure the blood pressure value of the subject 2. The measuring apparatus 10 of the blood pressure measuring system 1 may be an apparatus which can invasively measure the blood pressure. Examples of such an apparatus are a patient monitor and a defibrillator. Of course, the measuring apparatus 10 may be configured so as to be able to measure various items (for example, an electrocardiogram, the respiration curve, the SpO2, and the body temperature) in addition to the invasive blood pressure.

In the example shown in FIG. 1, the arterial blood pressure is measured, and a catheter (arterial needle) 21 is inserted into the radial artery of the subject 2. A transducer 22 is fixed at the level of the heart (the level corresponding to a half of the chest depth) of the subject 2. The catheter 21 and the transducer 22 are connected to each other through a monitoring line 23.

The monitoring line 23 includes a first tube 23a, a second tube 23b, a third tube 23c, a three-way stopcock 23d, and an infusion bottle 23e. The first tube 23a connects the catheter 21 to the three-way stopcock 23d. The second tube 23b connects the transducer 22 to the three-way stopcock 23d. When the blood pressure is to be measured, the three-way stopcock 23d connects the first tube 23a to the second tube 23b to isolate the interiors of the tubes from the atmosphere. When the zero point calibration is to be performed, the three-way stopcock 23d performs a plugging operation so as to cause the transducer 22 to be in contact with the atmosphere. The third tube 23c connects the infusion bottle 23e to the transducer 22. The infusion bottle 23e stores a physiological saline solution.

The transducer 22 is a converting device which is used in the invasive blood pressure measurement. The transducer 22 outputs an electrical signal corresponding to the pressure in the blood vessel of the subject 2, the pressure being transmitted through the physiological saline solution. The measuring apparatus 10 displays the blood pressure value and waveform corresponding to the electrical signal, to the user such as a medical person.

The measuring apparatus 10 includes a controller 11, a notifying section 16, an inputting section 17, and a displaying section 18. The controller 11 includes a measuring section 12, a detector 13, a notification controller 14, and a calibrator 15. Furthermore, the controller 11 appropriately includes a secondary storage device which is not shown, and the like.

The notifying section 16 outputs voice guidance or an alarm, and is configured, for example, by a speaker, a peripheral circuit for the speaker, and the like. The notifying section 16 is not limited to a sound outputting device, and may be configured, for example, by a device for visually notifying an alarm, such as an indicator. The outputting process of the notifying section 16 is controlled by the notification controller 14 which will be described later.

The inputting section 17 is an interface for receiving a data input performed by the medical person. For example, the inputting section 17 is configured by buttons, knobs, switches, or the like which are disposed on the case of the measuring apparatus 10. Alternatively, the inputting section 17 may have a configuration in which the inputting section is integrated with a display (a liquid crystal display), as in a touch panel. The inputting section 17 includes buttons for zero point calibration, and all zeroing which will be described later.

The displaying section 18 is configured by a displaying device for displaying various measurement values and display messages of the measuring apparatus 10, and peripheral circuits (or software). The displaying section 18 may be a liquid crystal display or indicator which is disposed on the case of the measuring apparatus 10, or a displaying device which is configured so as to be attachable to and detachable from the measuring apparatus 10.

Then, the functions of the various processing sections in the controller 11 will be described. The controller 11 controls the measuring apparatus 10, appropriately reads out a program from the memory (secondary storage device) which is not illustrated, and executes it. The controller 11 performs a display control and the like in execution of, for example, the zero point calibration.

The calibrator 15 calibrates a measurement reference value of the blood pressure value which is to be measured by the measuring apparatus 10. At the timing of start of the blood pressure measurement, for example, the zero point calibration is performed on the measuring apparatus 10. Specifically, the three-way stopcock 23d is set to be opened to the atmosphere to make the pressure acting on the transducer 22 zero. In this state, the calibrator 15 performs an internal calibration so that the electrical signal supplied to the measuring apparatus 10 has a reference value (for example, 0 mmHg).

The measuring section 12 performs an invasive blood pressure measurement. Namely, the measuring section 12 converts the electrical signal output from the transducer 22 to digital data by means of an A/D conversion process, and calculates the blood pressure value and the blood pressure waveform based on the converted digital value. The methods of calculating the blood pressure value and the blood pressure waveform may be similar to the technique used in a usual invasive blood pressure measurement. The calculated blood pressure value and waveform are displayed on the displaying section 18.

Moreover, the measuring section 12 detects, during the measurement, that the blood pressure enters a predetermined abnormal condition. Based on the calculated blood pressure value and waveform, for example, the measuring section detects that the predetermined abnormal condition occurs in the subject 2. The predetermined abnormal condition in this case is a condition which is caused, for example, when the catheter 21 attached to the subject is detached. For example, a condition in which there is no pulse, and the mean blood pressure is 100 mmHg or lower is continued for a predetermined time period (for example, about 10 seconds). Also in the case where the blood pressure devices are in the occluded state, and the output blood pressure value exceeds a threshold (for example, 200 to 300 mmHg) which is set in the measuring apparatus 10, it is detected that the predetermined abnormal condition occurs.

The detector 13 detects whether the zero point calibration is being executed or not. The detector 13 further detects a predetermined timing relating to the zero point calibration. The detection results are notified in real time from the detector 13 to the notification controller 14. By using the technique shown in (1) to (3) below, for example, the detector 13 determines whether the zero point calibration is being executed or not, or whether it is the predetermined timing relating to the zero point calibration or not.

(1) Depression of "Zero Point Calibration/all Zeroing" Button

The detector 13 monitors the input interface (a button, a knob, a switch, or the like) relating to the zero point calibration, and, if an operation indicative of execution of the zero point calibration is performed, determines that the zero point calibration is being executed.

(2) Execution of Process of Zero Point Calibration

The detector 13 monitors the operation of the calibrator 15, and, if it is detected that the zero point calibration is performed (for example, software for the zero point calibration is executed), determines that the zero point calibration is being executed. Similarly, the detector 13 monitors the operation of the calibrator 15, and, if it is detected that the zero point calibration is ended (for example, the software for the zero point calibration is ended), determines that the zero point calibration is ended.

(3) Display of Message Relating to Zero Point Calibration

The detector 13 monitors displaying instruction which is issued from the calibrator 15 to the displaying section 18, and which relates to the execution of the zero point calibration, or a message display process which is performed on the displaying section 18, and which relates to the execution of the zero point calibration. If the display of a message indicating that the zero point calibration is being executed is detected, the detector 13 determines that the zero point calibration is being executed. Also in the case where the display of a zero point calibration screen on the displaying section 18 is detected, moreover, the detector 13 determines that the zero point calibration is being executed. In the case where a display of an end message relating to the zero point calibration is detected, the detector 13 determines that the zero point calibration is ended.

(4) Detection of all Zeroing Operation

A detection method relating to all zeroing is used in the case where an invasive blood pressure measurement is performed in a plurality of portions by using a plurality of catheters 21. In the case where an all zeroing operation (an operation of performing the zero point calibration in a plurality of portions) by using software is detected, the detector 13 determines that the zero point calibration is being executed.

The notification controller 14 controls the alarm output which is performed by the notifying section 16, based on the detection state of the zero point calibration which is executed by the detector 13, and that of the predetermined abnormal condition which is performed by the measuring section 12. Moreover, the notification controller 14 selects an output mode of the alarm based on the elapsed time period from the predetermined timing relating to the zero point calibration, and the blood pressure value and waveform output from the measuring section 12.

The predetermined timing corresponds, for example, to timings indicated in following (A) to (F):

(A) a timing when the interface for "zero point calibration" or "all zeroing" is operated;

(B) a timing when the display of a message relating to the execution of the zero point calibration is started;

(C) a timing when the zero point calibration is ended;

(D) a timing when the display of a message relating to the end of the zero point calibration is started;

(E) a timing when the display of the message relating to the end of the zero point calibration is ended; and (F) a timing when the predetermined abnormal condition is started.

These predetermined timings are detected by the detector 13.

Next, an operation example of the measuring apparatus 10 in the blood pressure measuring system 1 will be described with reference to FIGS. 2 to 6. In the example, an operation in the case where the zero point calibration is performed on the measuring apparatus 10 at start of the blood pressure measurement will be described.

Figure 2:
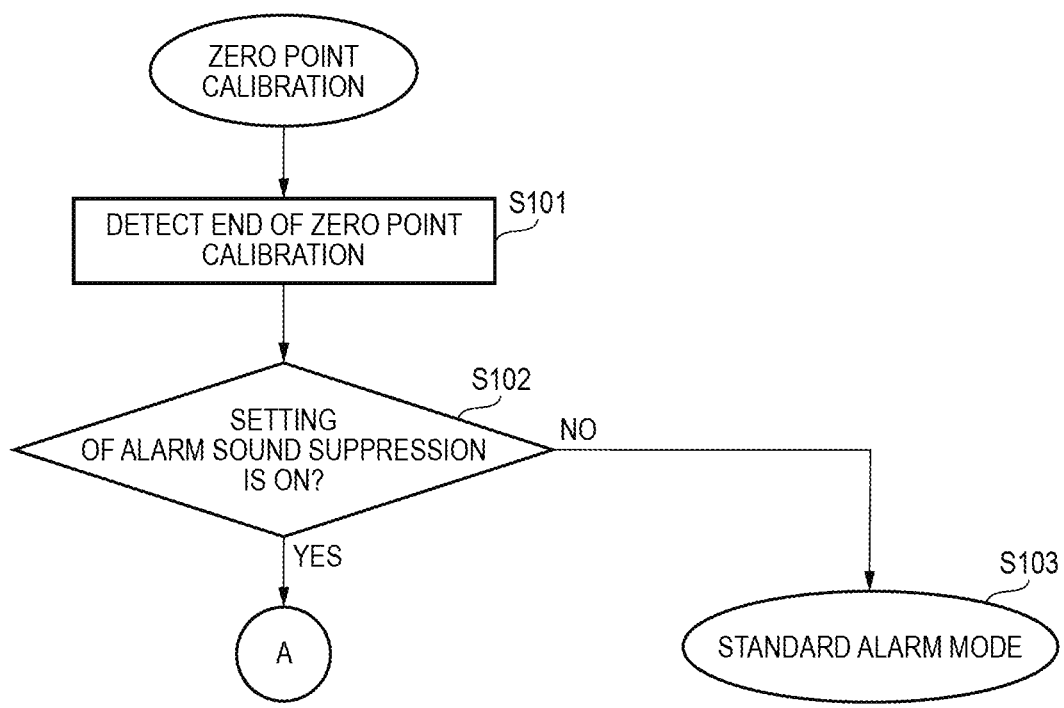
FIG. 2 is a flowchart illustrating the operation of the measuring apparatus.

When, for example, a zero point calibration button in the measuring apparatus 10 is depressed, as shown in FIG. 2, the detector 13 detects that the zero point calibration is started. When, for example, the software for the zero point calibration is ended, moreover, the detector 13 detects that the zero point calibration is ended (step S101). In the example, the timing when the zero point calibration is ended is set as the above-described predetermined timing relating to the zero point calibration.

Then, the measuring apparatus 10 determines whether a setting switch for using an alarm sound suppression mode in which the alarm sound is suppressed is set to the ON state or not (step S102). If the determination result is that the setting switch is not set to the mode in which the alarm sound is suppressed, a state where a standard alarm mode (an example of the first mode) is selected is set (step S103). In the example, the standard alarm mode is a mode in which, in the case where the predetermined abnormal condition is detected, an alarm message is displayed, and the alarm sound is output.

Regardless of the ON/OFF state of the setting switch, the measuring apparatus 10 of the embodiment is set so that, during a period from the end of the zero point calibration to, for example, the 30 second elapse, the alarm message is not displayed, and the alarm sound is not output (sounded) even in the case where the predetermined abnormal condition is detected.

By contrast, if it is determined in step S102 that the setting switch is set to the mode in which the alarm sound is suppressed, the notification controller 14 checks at a timing when, for example, 30 seconds have elapsed from the end of the zero point calibration, whether the alarm sound suppression mode (an example of the second mode) is to be selected or not.

The alarm sound suppression mode is a mode in which, in the case where the predetermined abnormal condition is detected, the alarm sound is suppressed by, for example, inhibiting the alarm sound from being output, or reducing the volume of the alarm sound to a level that is lower than the volume level in the standard alarm mode. The alarm message may not or may be displayed.

Figure 3:
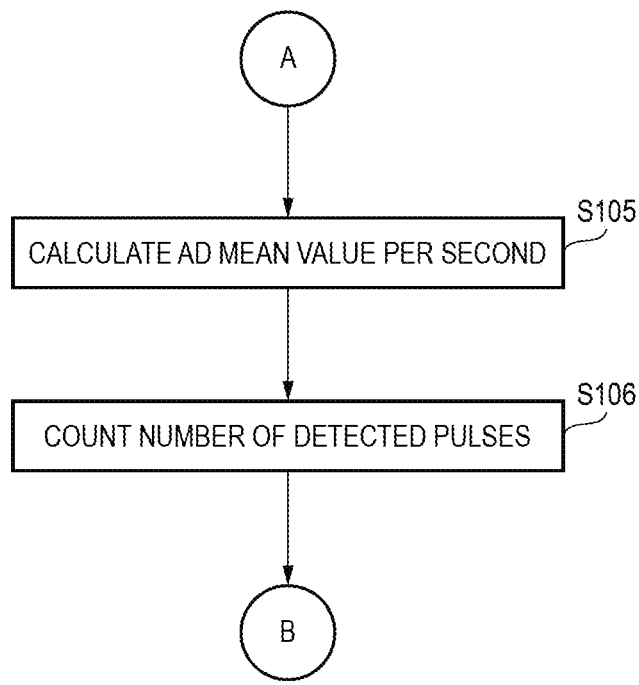
FIG. 3 is a flowchart illustrating the operation of the measuring apparatus.

As shown in FIG. 3, then, the measuring section 12 calculates the blood pressure value under measurement based on the electrical signal which is output from the transducer 22 (step S105). The blood pressure value is the mean blood pressure value which is obtained by averaging the value output from the transducer 22, over one second.

The measuring section 12 counts the number of the detected pulses (step S106).

For example, the calculation of the blood pressure value, and the counting of the pulse number are processes which are started after the end of the zero point calibration, and which are thereafter performed repeatedly and continuously.

Figure 4:
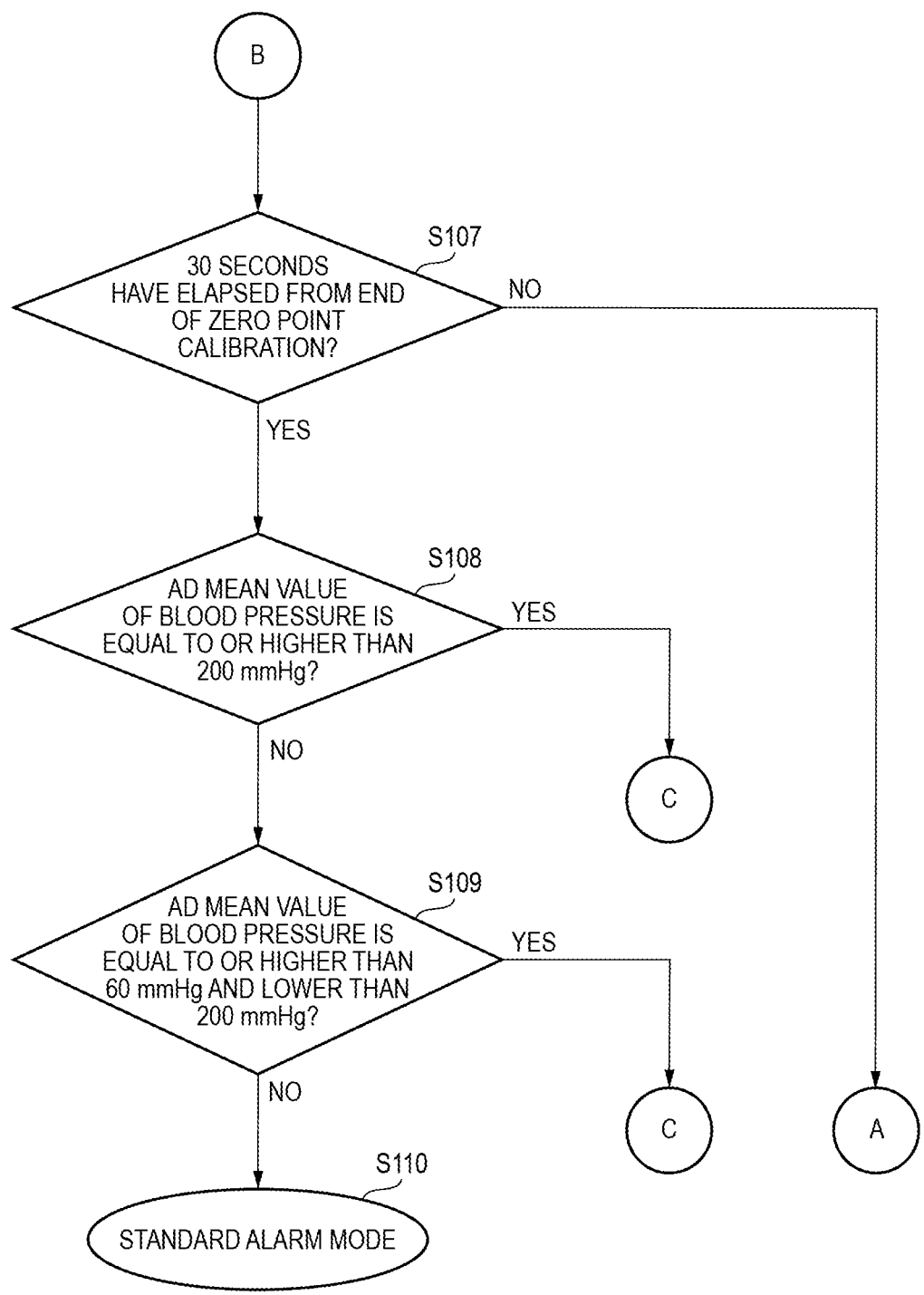
FIG. 4 is a flowchart illustrating the operation of the measuring apparatus.

As shown in FIG. 4, then, the notification controller 14 determines whether 30 seconds have elapsed from the end of the zero point calibration or not (step S107). If it is determined that 30 seconds have not elapsed, the control returns to step A in FIG. 3, and the process are repeated.

By contrast, it is determined that 30 seconds have elapsed, the notification controller 14 determines whether or not the blood pressure value calculated by the measuring section 12 is equal to or higher than a second set value (for example, 200 mmHg) which is previously set (step S108). The second set value may be set in the range of 150 to 300 mmHg. In the example, a first set value which will be described later is set to 60 mmHg. The first set value is set to 60 mmHg in order to prevent the measurement of the venous pressure in which pulsation does not appear, from being disturbed.

If it is determined in step S108 that the blood pressure value is not equal to or higher than 200 mmHg, the notification controller 14 determines whether the blood pressure value is equal to or higher than the first set value (for example, 60 mmHg) and lower than the second set value (200 mmHg) or not (step S109). If the blood pressure value is not equal to or higher than 60 mmHg and lower than 200 mmHg, that is, the blood pressure value is lower than 60 mmHg, the notification controller 14 selects the standard alarm mode (step S110).

Figure 5:
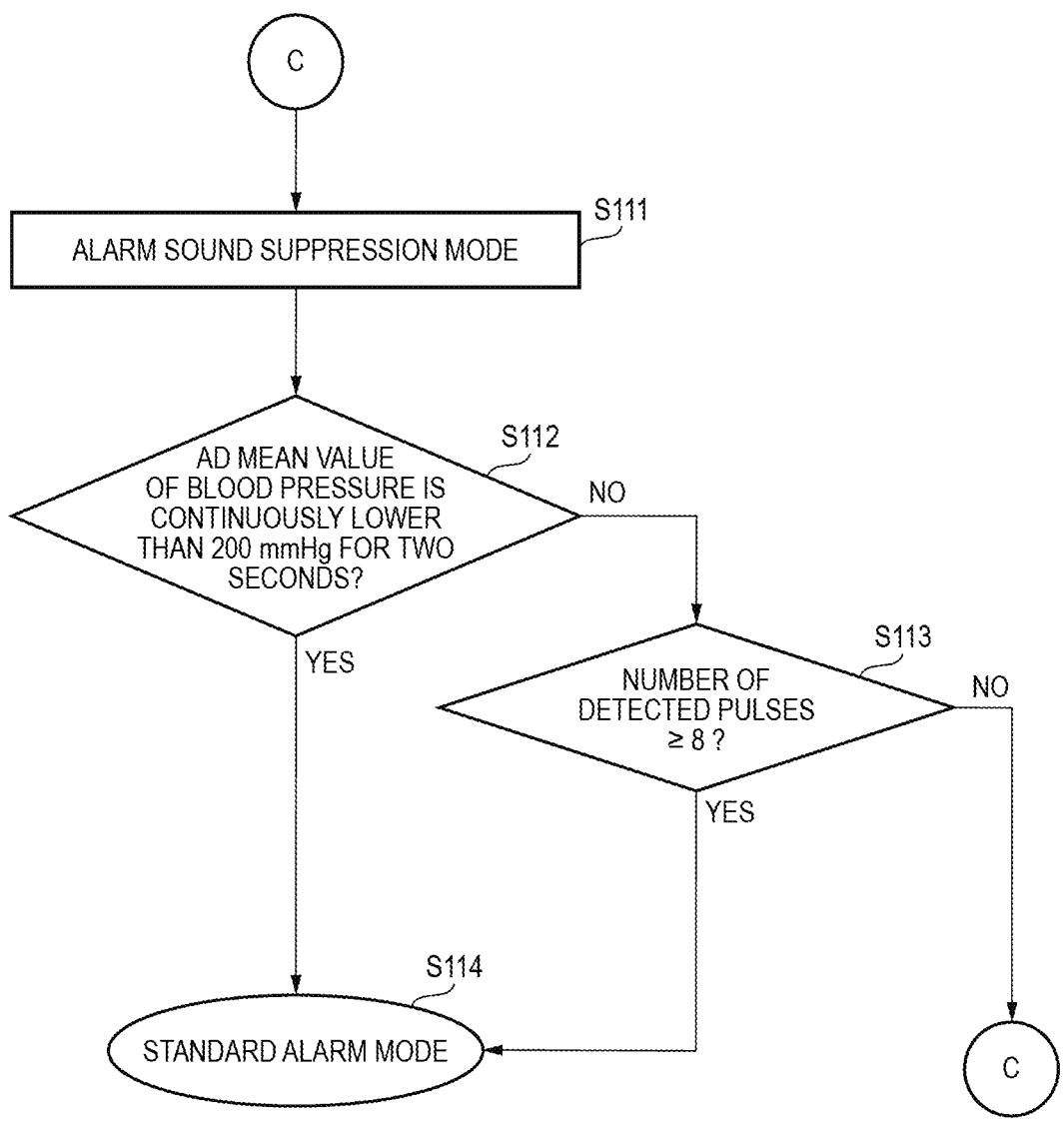
FIG. 5 is a flowchart illustrating the operation of the measuring apparatus.

By contrast, it is determined in step S108 that the blood pressure value is equal to or higher than 200 mmHg, the notification controller 14 selects the alarm sound suppression mode as shown in FIG. 5 (step S111).

Then, the notification controller 14 determines whether or not the blood pressure value under measurement is continuously lowered to less than 200 mmHg for 2 seconds or longer (step S112). If it is determined that the blood pressure value under measurement is not continuously lowered to less than 200 mmHg for 2 seconds or longer, that is, the blood pressure value is maintained to 200 mmHg or higher, the notification controller 14 determines whether the pulse is continuously detected for eight beats or more (step S113). A pulse of continuous eight beats means a pulse in which the time period between beats is equal to or shorter than two seconds, and which continues for eight beats. The number of pulses is set to eight while considering the number of pulses which can be measured as the physiological signal of the subject. If it is determined that the number of the detected pulses is smaller than eight beats, the control returns to step S111, and the alarm sound suppression mode is maintained. In the case where the situation where the blood pressure value under measurement is maintained to 200 mmHg or higher, and the number of detected pulses is smaller than eight beats is continued, the alarm sound suppression mode is continued and prolonged without being limited by the elapsed time period.

By contrast, in the case where it is determined in step S112 that the blood pressure value is continuously lowered to less than 200 mmHg for 2 seconds or longer, the notification controller 14 selects the standard alarm mode (step S114). Also in the case where it is determined in step S113 that a pulse of eight beats or more is detected, the notification controller 14 selects the standard alarm mode (step S114).

Figure 6:
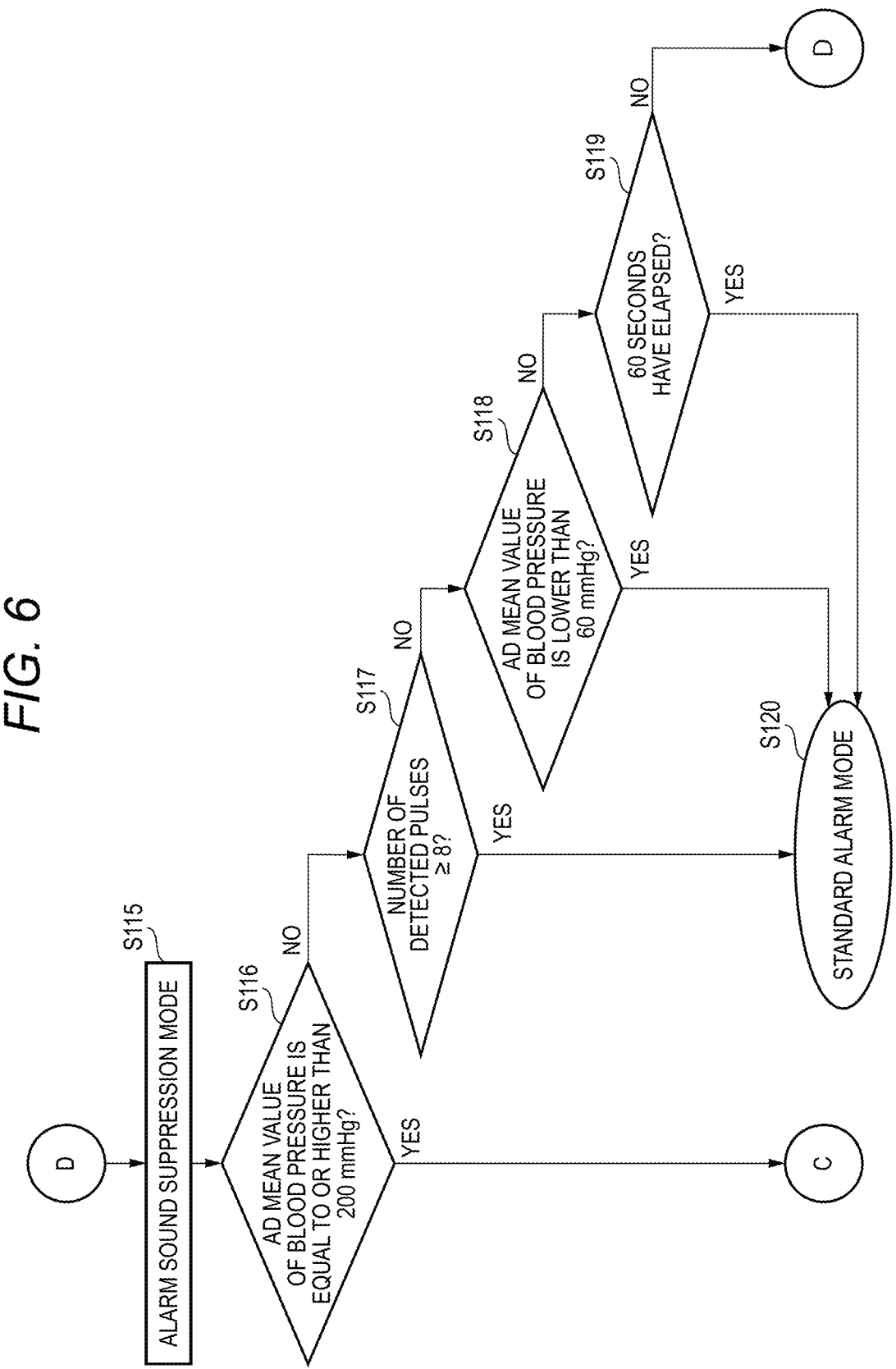
FIG. 6 is a flowchart illustrating the operation of the measuring apparatus.

Returning to FIG. 4, in the case where it is determined in step S109 that the blood pressure value is equal to or higher than 60 mmHg and lower than 200 mmHg, the notification controller 14 selects the alarm sound suppression mode as shown in FIG. 6 (step S115).

Then, the notification controller 14 determines whether the blood pressure value is raised to 200 mmHg or higher or not (step S116). If it is determined that the blood pressure value is not raised to 200 mmHg or higher, that is, the blood pressure value is equal to or higher than 60 mmHg and lower than 200 mmHg, the notification controller 14 determines whether or not the pulse is continuously detected for eight beats or more (step S117). If it is determined that the number of the detected pulses is smaller than eight beats, the notification controller 14 determines whether or not the blood pressure value is lowered to 60 mmHg or less (step S118). If it is determined that the blood pressure value is not lowered to 60 mmHg or less, the notification controller 14 determines whether 60 seconds (an example of the second set time period) have elapsed in total from the end of the zero point calibration or not (step S119). If it is determined that 60 seconds have not elapsed, the control returns to step S115, the processes are repeated, and the alarm sound suppression mode is maintained.

By contrast, in the case where it is determined in step S116 that the blood pressure value is raised to 200 mmHg or higher, the control returns to step S111 of FIG. 5, and the processes are repeated.

In the case where it is determined in step S117 that the pulse is detected for eight beats or more, the notification controller 14 selects the standard alarm mode (step S120).

Also in the case where it is determined in step S118 that the blood pressure value is lowered to less than 60 mmHg, the notification controller 14 selects the standard alarm mode (step S120).

Also in the case where it is determined in step S119 that the elapsed time period reaches 60 seconds, the notification controller 14 selects the standard alarm mode (step S120).

A part or all of the processes of the controller 11 in the measuring apparatus 10 can be realized as computer programs which operate in the measuring apparatus 10. For example, the measuring section 12 can calculate the blood pressure value and the blood pressure waveform with using data which are obtained by digitizing the electrical signals output from the transducer 22 by the A/D conversion process.

The programs may be stored by using a non-transitory computer readable medium of any one of various types, and then supplied to the computer. The non-transitory computer readable medium includes tangible storage media of various types. Examples of the non-transitory computer readable medium are a magnetic recording medium (for example, a flexible disk, a magnetic tape, and a hard disk drive), a magneto-optical recording medium (for example, a magneto-optical disk), a CD-ROM (Read Only Memory), a CD-R, a CD-R/W, and a semiconductor memory (for example, a mask ROM, a PROM (Programmable ROM), an EPROM (Erasable PROM), a flash ROM, and a RAM (random access memory)). Alternatively, the programs may be supplied to the computer by means of a transitory computer readable medium of any one of various types. Examples of the transitory computer readable medium include an electrical signal, an optical signal, and an electromagnetic wave. The transitory computer readable medium can supply the programs to the computer through a wired communication path such as an electric wire or an optical fiber, or a wireless communication path.

In a measuring apparatus which can invasively measure the blood pressure value, in order to allow the blood pressure waveform and value to be immediately displayed at the timing when, after blood pressure devices are assembled, the blood pressure line of the subject is ensured, a situation sometimes occurs where the zero point calibration is previously performed, and the blood pressure devices are set to the occluded state, and wait for measurement.

Figure 7:
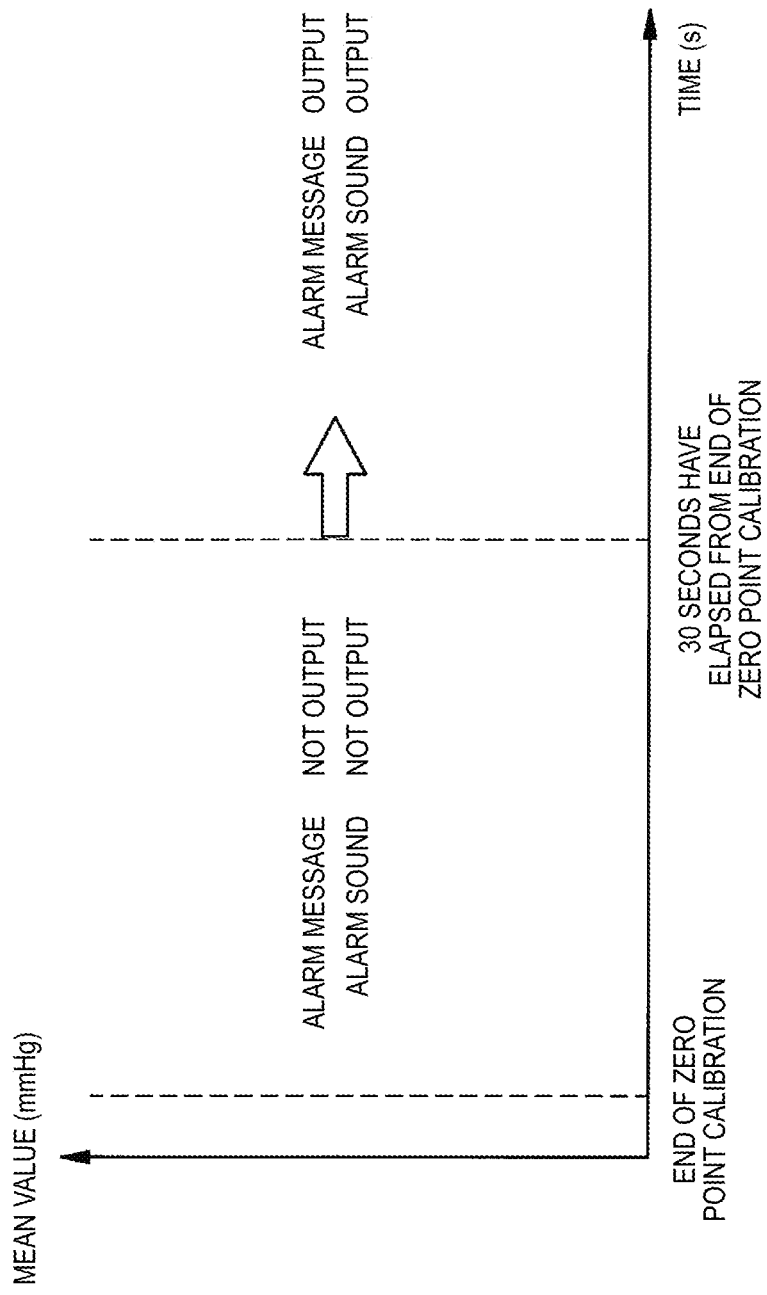
FIG. 7 is a conceptual view showing an example of alarm mode switching in a related-art measuring apparatus.

However, a related-art measuring apparatus has a configuration where, subject only to the elapsed time period (30 seconds) from the end of the zero point calibration, a mode in which an alarm sound and an alarm message are not output is switched to that in which the alarm sound and the alarm message are output, as shown in FIG. 7.

In the case where, because of preparation of a surgical operation or the like, the occluded state is continued after an elapse of a predetermined time period (30 seconds) from the end of the zero point calibration, therefore, a situation sometimes occurs where the pressure in the blood pressure circuit becomes high to exceed a threshold which is set in the measuring apparatus, and an alarm sound (clinically, an error alarm) is generated.

In the following cases, for example, a so-called wasteful generation of an alarm sound occurs:

1) the case where the zero point calibration is performed during a preparation period before a surgical operation, and flashing and closure of a three-way stopcock are performed;

2) before the subject enters the operating room; and 3) the case where, after completion of the zero point calibration, a time period for ensuring the intra-arterial line (A line) is prolonged.

By contrast, the measuring apparatus 10, blood pressure measuring method, and program in the embodiment have the alarm sound suppression mode (the example of the second mode) which is selected in the case where predetermined conditions are satisfied, in addition to the standard alarm mode (the example of the first mode) in which the alarm sound and the alarm message are output. For example, the predetermined conditions are configured by using the elapsed time from the end (predetermined timing) of the zero point calibration, and the output of the measuring section. When the predetermined conditions are set so as to correspond to an expected artifact state, i.e., noises which are mixable into an electrocardiogram, occurrence of a so-called wasteful generation of an alarm sound can be reduced, and the alarm sound can be output at an appropriate timing. In the case where the predetermined conditions are not satisfied (in the case where it can be determined that the physiological signal of the subject is measured), the standard alarm mode is selected, and the mode is transferred from the alarm sound suppression mode to the standard alarm mode, thereby allowing the alarm sound to be output.

Figure 8:
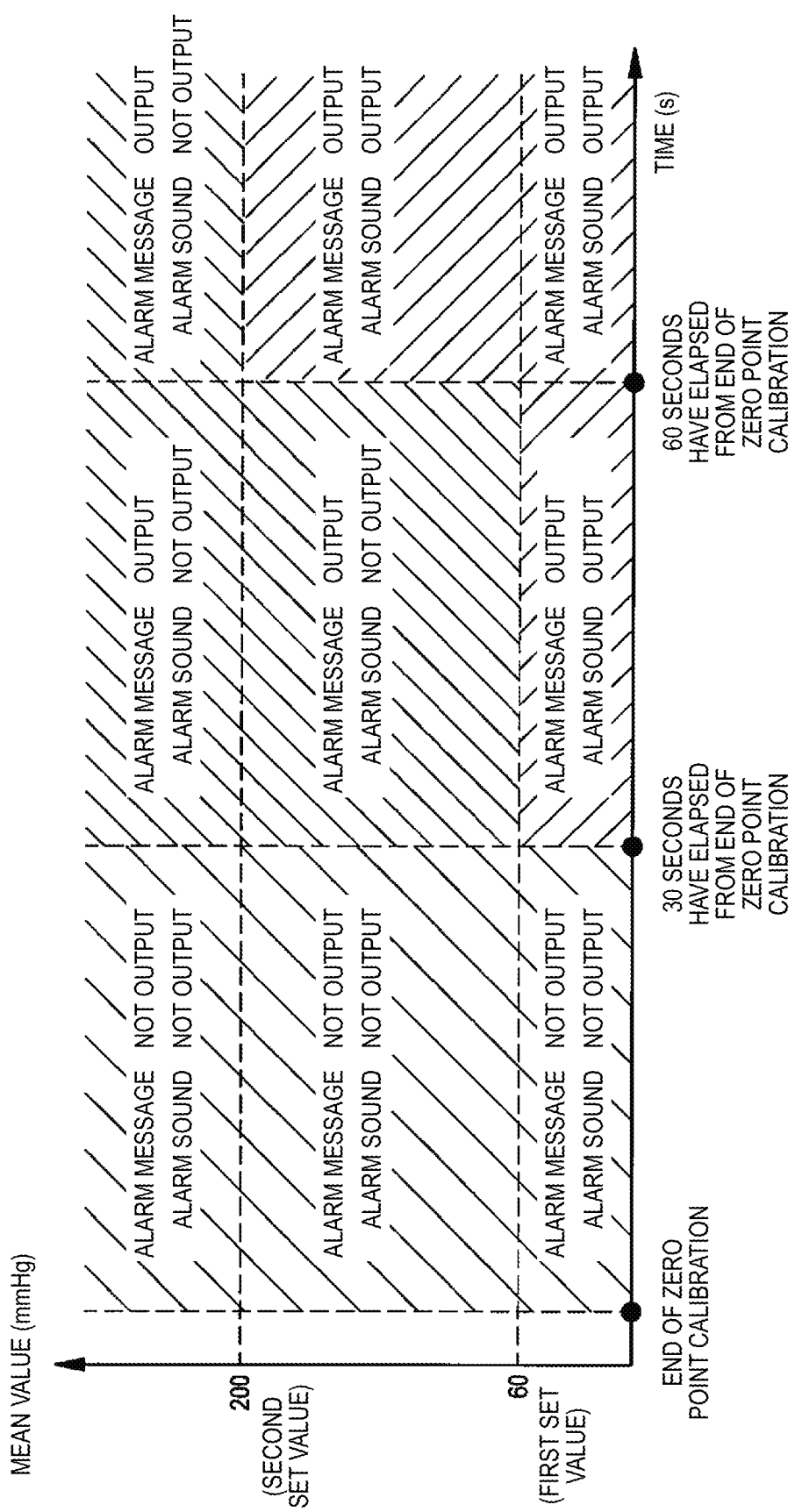
FIG. 8 is a conceptual view showing an example of alarm mode switching in the measuring apparatus of the embodiment.

FIG. 8 is a conceptual view illustrating an example of alarm mode switching along the time sequence. In the example, for example, a mode in which the alarm sound and the alarm message are not output is performed irrespective of the output conditions of the measuring section during a period from the end of the zero point calibration to an elapse of 30 seconds thereafter as shown in FIG. 8.

In the case where the blood pressure value is lower than 60 mmHg at a timing (in the first set time period) when 30 seconds have elapsed from the end of the zero point calibration, the standard alarm mode is selected. In the time period after the timing, the standard alarm mode is continued irrespective of the output conditions of the measuring section.

In the case where the blood pressure value is equal to or higher than 60 mmHg and lower than 200 mmHg, or equal to or higher than 200 mmHg at the timing when 30 seconds have elapsed from the end of the zero point calibration, the alarm sound suppression mode is selected.

During a period from the end of the zero point calibration to a timing when 30 seconds have further elapsed (from the end of the zero point calibration to a timing when 60 seconds have elapsed), in the case where the blood pressure value is equal to or higher than 60 mmHg and lower than 200 mmHg, and the number of the detected pulses is equal to or larger than eight beats, the mode is transferred from the alarm sound suppression mode to the standard alarm mode (see S116, S117, and S120 in FIG. 6).

Also in the case where the blood pressure value which has been equal to or higher than 60 mmHg and lower than 200 mmHg is lowered to less than 60 mmHg, similarly, the mode is transferred from the alarm sound suppression mode to the standard alarm mode (see S116, S117, S118, and S120 in FIG. 6).

In the case where the blood pressure value is equal to or higher than 200 mmHg, and the number of the detected pulses is smaller than eight beats, the alarm sound suppression mode is maintained (see S112 and S113 in FIG. 5).

In the case where the blood pressure value is equal to or higher than 200 mmHg, and the number of the detected pulses is equal to or larger than eight beats, the mode is transferred from the alarm sound suppression mode to the standard alarm mode (see S112, S113, and S114 in FIG. 5). Also in the case where the blood pressure value which has been equal to or higher than 200 mmHg is continued to be lower than 200 mmHg for two seconds, the mode is transferred from the alarm sound suppression mode to the standard alarm mode (see S112 and S114 in FIG. 5).

In the case where the blood pressure value is equal to or higher than 60 mmHg and lower than 200 mmHg at a timing (in the second set time period) when 60 seconds have elapsed from the end of the zero point calibration, the mode is transferred from the alarm sound suppression mode to the standard alarm mode. In the time period after the timing, the standard alarm mode is continued irrespective of the output conditions of the measuring section.

In the case where the blood pressure value is equal to or higher than 200 mmHg at the timing when 60 seconds have elapsed from the end of the zero point calibration, the alarm sound suppression mode is continued.

In the time period after the timing when 60 seconds has elapsed from the end of the zero point calibration, in the case where the blood pressure value is equal to or higher than 200 mmHg, and the number of the detected pulses is smaller than eight beats, the alarm sound suppression mode is continued (see S112 and S113 in FIG. 5).

In the case where the blood pressure value is equal to or higher than 200 mmHg, and the number of the detected pulses is equal to or larger than eight beats, the mode is transferred from the alarm sound suppression mode to the standard alarm mode (see S112, S113, and S114 in FIG. 5). Also in the case where the blood pressure value which has been equal to or higher than 200 mmHg is continued to be lower than 200 mmHg for two seconds, the mode is transferred from the alarm sound suppression mode to the standard alarm mode (see S112 and S114 in FIG. 5).

Figure 9:
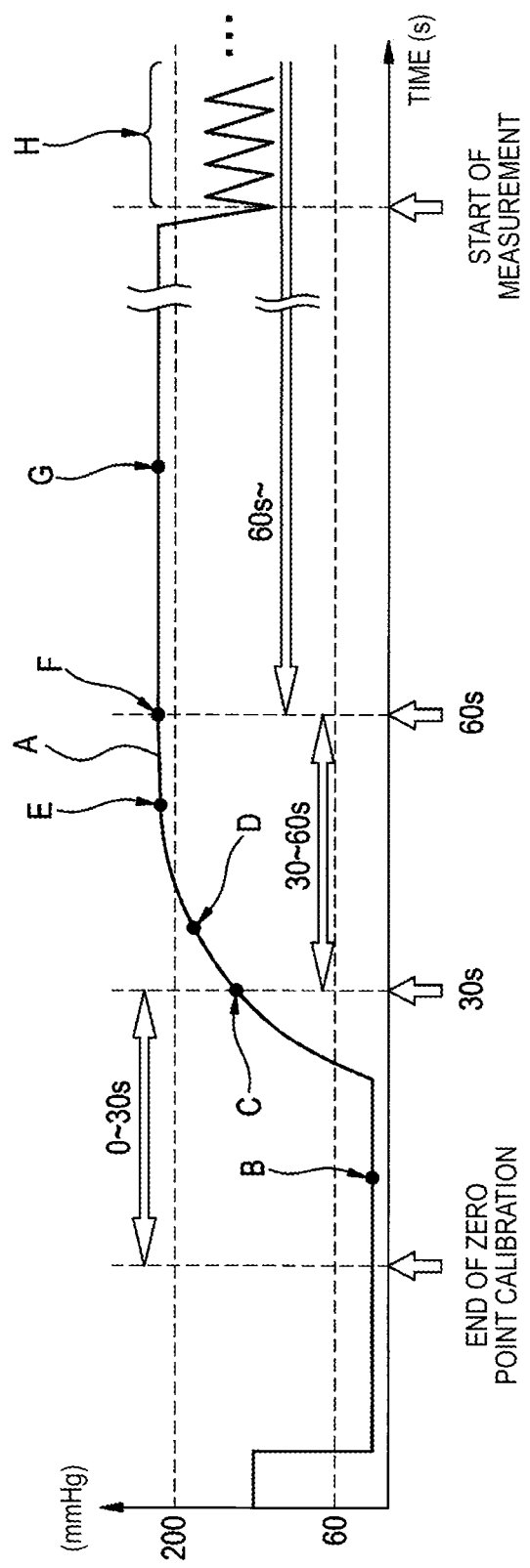
FIG. 9 is a view illustrating an example of alarm mode switching.

The operation of the measuring apparatus 10 will be described by way of an example (FIG. 9) of a blood pressure waveform which can be measured during the zero point calibration. The blood pressure waveform A illustrated in FIG. 9 is an example of a waveform which is measured in the case where waiting is performed while the blood pressure devices are set to the occluded state after the end of the zero point calibration.

In the example, as described above, the mode in which both the alarm sound and the message are not output is executed during 30 seconds after the end of the zero point calibration. During this time period, therefore, the alarm sound is not output even when the pressure acting on the transducer 22 is substantially zero, and the blood pressure value of the blood pressure waveform A is in the predetermined abnormal condition (condition of 10 mmHg or lower) as in point B indicated by the arrow.

At the timing when 30 seconds have elapsed from the end of the zero point calibration, the blood pressure value of the blood pressure waveform A is equal to or higher than 60 mmHg and lower than 200 mmHg as in point C, and therefore the alarm sound suppression mode is selected.

During the period from the 30 second elapse from the end of the zero point calibration to the 60 second elapse, the blood pressure value of the blood pressure waveform A is equal to or higher than 60 mmHg and lower than 200 mmHg (point D) or equal to or higher than 200 mmHg (point E), and furthermore no pulse is detected in the example (because waiting is performed while the blood pressure devices are set to the occluded state). Therefore, the above-described alarm sound suppression mode is maintained.

At the timing when 60 seconds have elapsed from the end of the zero point calibration, the blood pressure value of the blood pressure waveform A is equal to or higher than 200 mmHg as in point F, and therefore the above-described alarm sound suppression mode is continued.

In the time period after the timing when 60 seconds have elapsed from the end of the zero point calibration, in the case where the blood pressure value of the blood pressure waveform A is equal to or higher than 200 mmHg as in point G, and a pulse is not detected, the above-described alarm sound suppression mode is continued. After the measurement of the blood pressure of the subject is started, in the case where the blood pressure value of the blood pressure waveform A is continued to be lower than 200 mmHg for two seconds as indicated in region H, the mode is transferred to the standard alarm mode.

Even in the case where the zero point calibration is performed, the apparatus can be selectively controlled as described above so that the alarm sound is output or suppressed at an appropriate timing. As a result, it is not necessary for the medical person to perform an operation of cancelling the alarm sound, and other preparation works are not disturbed.

Moreover, one of the plurality of timings relating to the zero point calibration can be used as the predetermined timing which functions as the reference for the mode selection. Therefore, it is possible adequately design the conditions for selecting the alarm sound suppression mode.

Even in the case where the alarm sound suppression mode is selected, and the output of the alarm sound is suppressed, the alarm message is displayed, and hence the predetermined abnormal condition can be checked by seeing the message.

The invention is not limited to the above-described embodiment, and may be adequately subjected to modification, improvement, and the like. In addition, the materials, shapes, dimensions, numerical values, forms, numbers, placement places, and the like of the components of the above-described embodiment are arbitrary and not limited insofar as the invention is achieved.

According to an aspect of the presently disclosed subject matter, there is provided a measuring apparatus comprising: a measuring section which is configured to perform an invasive blood pressure measurement, and which is configured to detect that a predetermined abnormal condition occurs in a blood pressure during the invasive blood pressure measurement; a detector which is configured to detect whether or not a zero point calibration is being executed on a transducer that is to be used in the invasive blood pressure measurement; and a notification controller which, in a case where the blood pressure measured by the measuring section is in the predetermined abnormal condition, is configured to control whether an alarm is output or not, based on a detection state of the detector, wherein the notification controller can select a first mode in which an alarm sound is output, or a second mode in which the alarm sound is not output, based on an elapsed time period from a predetermined timing relating to the zero point calibration, and an output from the measuring section.

According to an aspect of the presently disclosed subject matter, there is also provided a blood pressure measuring method comprising: performing an invasive blood pressure measurement, and detecting that a predetermined abnormal condition occurs in a blood pressure during the invasive blood pressure measurement; detecting whether or not a zero point calibration is being executed on a transducer that is to be used in the invasive blood pressure measurement; and in a case where the blood pressure is in the predetermined abnormal condition, controlling whether an alarm is output or not, based on a detection state, and, in the controlling, a first mode in which an alarm sound is output, or a second mode in which the alarm sound is not output is selected based on an elapsed time period from a predetermined timing relating to the zero point calibration, and an output in the measuring step.

According to the above configurations, in the case where the elapsed time period from the predetermined timing relating to the zero point calibration, and the output from the measuring section satisfy predetermined conditions, it is possible to select the second mode where the alarm sound is not output, and therefore the alarm sound can be prevented from being wastefully generated. In the case where the predetermined conditions are not satisfied, the first mode where the alarm sound is output is selected, and the alarm sound is generated.

According to the above configurations, even in the case where the zero point calibration is performed, consequently, it is possible to, at an appropriate timing, allow or suppress an output of an alarm sound. As a result, the medical person is not required to perform an operation of cancelling an alarm sound, and other preparation works are not disturbed.

According to the measuring apparatus and the blood pressure measuring method of the presently disclosed subject matter, an alarm sound can be adequately output even in the case where the zero point calibration is performed.

What is claimed is:

1. A measuring apparatus comprising:
at least one controller configured to:
perform an invasive blood pressure measurement;
detect that a predetermined abnormal condition occurs in a blood pressure during the invasive blood pressure measurement;
detect whether or not a zero point calibration is being executed on a transducer that is used in the invasive blood pressure measurement; and
when the measured blood pressure is in the predetermined abnormal condition, control whether an alarm is output or not, based on a state of the detection of execution of the zero point calibration,
wherein the controller is configured to select a first mode in which an alarm sound and an alarm message are output, a second mode in which the alarm sound is not output and the alarm message is output, or a third mode in which an alarm sound and an alarm message are not output, based on an elapsed time period from a predetermined timing relating to the zero point calibration, and based on the invasive blood pressure measurement,
wherein the elapsed time period has an initial set time period, a first set time period that is after the initial set time period, and a second set time period that is after the first set time period,
wherein the controller is configured to select the third mode during the initial set time period,
wherein when, during the first set time period, a blood pressure under measurement is lower than a first set value, the controller is configured to select the first mode, and
wherein when, during the first set time period, the blood pressure under measurement is between the first set value and a second set value that is larger than the first set value, the controller is configured to select the second mode.

2. The measuring apparatus according to claim 1, wherein the predetermined timing is one of:
a timing of operating an interface relating to the zero point calibration; a timing of starting a display of a message relating to execution of the zero point calibration; a timing of an end of the zero point calibration; a timing of starting a display of a message relating to the end of the zero point calibration; and a timing of ending the display of the message relating to the end of the zero point calibration.

3. The measuring apparatus according to claim 1, wherein, when, during the first set time period, the blood pressure under measurement is higher than the second set value, the controller is configured to select the second mode.

4. The measuring apparatus according to claim 3, wherein, when, during the second set time period, the blood pressure under measurement is higher than the second set value, the controller is configured to continue the second mode.

5. The measuring apparatus according to claim 1, wherein, when, during the second set time period, the blood pressure under measurement is between the first set value and a second set value that is larger than the first set value, the controller is configured to select the first mode.

6. A blood pressure measuring method comprising, with the measuring apparatus of claim 1:
- performing the invasive blood pressure measurement, and detecting that the predetermined abnormal condition occurs in the blood pressure during the invasive blood pressure measurement;
- detecting whether or not the zero point calibration is being executed on the transducer that is used in the invasive blood pressure measurement; and
- when the measured blood pressure is in the predetermined abnormal condition, controlling whether an alarm is output or not, based on the detection state of execution of the zero point calibration,
- wherein in the controlling, the first mode in which the alarm sound and the alarm message are output, the second mode in which the alarm sound is not output and the alarm message is output, or the third mode in which the alarm sound and the alarm message are not output, is selected based on the elapsed time period from the predetermined timing relating to the zero point calibration, and based on the invasive blood pressure measurement,
- wherein the elapsed time period has the initial set time period, the first set time period that is after the initial set time period, and the second set time period that is after the first set time period,
- wherein the third mode is selected during the initial set time period,
- wherein the first mode is selected when, during the first set time period, the blood pressure under measurement is lower than the first set value, and
- wherein the second mode is selected when, during the first set time period, the blood pressure under measurement is between the first set value and the second set value that is larger than the first set value.

* * * * *